United States Patent [19]

Sredni et al.

[11] Patent Number: 4,946,437

[45] Date of Patent: Aug. 7, 1990

[54] METHOD FOR THE STIMULATION OF BONE MARROW CELLS

[75] Inventors: Benjamin Sredni, Beni Brak; Michael Albeck, Ramat Gan, both of Israel

[73] Assignee: Bar-Ilan University, Ramat-Gan, Israel

[21] Appl. No.: 278,957

[22] Filed: Dec. 2, 1988

[51] Int. Cl.$^5$ ............................................ A61M 31/00
[52] U.S. Cl. ........................................ 604/49; 604/48; 604/20
[58] Field of Search ...................................... 604/48–49

[56] References Cited

U.S. PATENT DOCUMENTS

| | | | |
|---|---|---|---|
| 4,481,946 | 11/1984 | Altshuler et al. | 604/28 |
| 4,486,188 | 12/1984 | Altshuler et al. | 604/7 |
| 4,752,614 | 6/1988 | Albeck et al. | |
| 4,761,490 | 8/1988 | Albeck et al. | 549/341 |
| 4,838,852 | 6/1989 | Edelson et al. | 604/4 |
| 4,861,704 | 8/1989 | Reemtsma et al. | 604/49 |

FOREIGN PATENT DOCUMENTS 0952189  8/1982  U.S.S.R. ............................. 604/49

OTHER PUBLICATIONS

Levay; Pharmac. Ther. A. pp. 223–229 (1976) Pergamon Press.
Martindale, Extra Pharmacopeia (1982).
Buscher; Zeitschrift Fur Naturforschung, vol. 36B (1981), pp. 307–312.
JACS vol. 103, No. 9 (1981), pp. 2340–2347; Denney et al.

*Primary Examiner*—Stephen C. Pellegrino
*Assistant Examiner*—Michael Rafa
*Attorney, Agent, or Firm*—Hedman, Gibson, Costigan & Hoare

[57] ABSTRACT

A novel method is disclosed for the stimulation of the differentiation of bone marrow cell which is based on the administration of an effective amount of a tellurium compound which has a stimulating effect on bone marrow cells.

6 Claims, No Drawings

METHOD FOR THE STIMULATION OF BONE MARROW CELLS

BACKGROUND OF THE INVENTION

A certain population of pluripotent stem-cells residing in the bone-marrow of adult mammalians have the potential to give rise to the large number of different hematopoietic cell types which circulate in the blood. Most of the red and white cells in the blood are short-lived and need to be replaced constantly throughout life. The process of blood formation is normally maintained in the bone-marrow at a high rate. The levels of mature cells in the circulation can change rapidly in response to different environmental stress ranging from blood loss, infections, etc.

The normal hematopoiesis is based on the dual functioning of a small population of multipotential stem cells. This is based on an extensive self-generating capacity which gives rise to new undifferentiated stem cells and on the ability of the stem cells to differentiate into the various cell lineages through multiple maturation stages giving rise to committed cells with limited capacity for cell division. The two main lines of differentiation from stems cells are the lymphoid lineage and the myeloid lineage.

The growth factors produced by the stromal cells located in the bone marrow regulate the number of self-replication multipotential stem cells. The division and differentiation of the committed cells is dependent on the continuous supply of specific glycoproteins regulating each of the hematopoietic lineages.

The myeloid lineage is controlled by a group of glycoproteins called colony stimulating factors (CSFs). In the murine system, four types of CSF were identified: multi-CSF (IL-3) exerts its effect on undifferentiated stem cells on precursors of granulocytes, macrophages, megakoryocytes, erythroid cells and in addition on basophils and mast cells. GM-CSF is a proliferative factor for macrophages eosinophils, neutrophils and also for megakaryocytes and erythroid cells in the presence of erythropoietin, G-CSF and M-CSF exert their effect on committed granulocytes, later in the maturation sequence.

Erythroid cells are controlled by burst promoting activity (BPA) in the earlier stages and by erythropoietin at the later stages of differentiation.

The megakaryocytic lineage is controlled by at least two factors: megakaryocytic colony stimulating activity (Meg - CSA) and thrombopoietin which regulates the early and more mature stages of the megakaryocytes respectively.

The lymphoid lineage gives rise to lymphoid progenitor with the potential to differentiate into either T or B cells. Precursors of T lymphocytes migrate to the thymus and become immunocompetent under the influences of thymic hormones. Then the T lymphocytes migrate to the lymphoid tissues where their activity is regulated by the T cell growth factor.

The process of hematopoiesis may be adversely affected by different diseases or by adverse environmental factors such as radiation.

Bone marrow transplants are used to provide a host with a healthy stem-cell population that is capable of differentiation into mature blood cells that will replace the hematopoietic cells of the host suffering from immunodeficiency syndromes, aplastic anemias and leukemias. Other indications for bone marrow transplants include hemoglobinopathies such as thalassemia and accidental exposure to high levels of radiation and chemotherapeutic treatments.

The marrow is obtained from a donor and may be incubated with monoclonal antibodies to T-lymphocytes prior to transplantation for the purpose of preventing graft versus host disease. Generally, no adjuvant is given in combination with the bone marrow transplant. The number of donors who match the recipients who require transplants is inadequate to meet the demand.

When a bone marrow transplant is carried out, from 3 to 5% of the bone marrow cells must be taken from the donor in order to provide the donee with a sufficient amount of cells that will establish a stem cell producing capability in the recipient. The scarcity of suitable donors limits the number of bone marrow transplants that may be carried out.

SUMMARY OF THE INVENTION

The present invention provides a method for the transplantation of bone marrow in a host in need of a bone marrow transplant. The method comprises:

(a) obtaining bone marrow cells;

(b) contacting said bone marrow cells with an amount of a compound which is:

(A) a source of tetravalent tellurium ions which is capable of inducing the proliferation or differentiation of bone marrow cells;

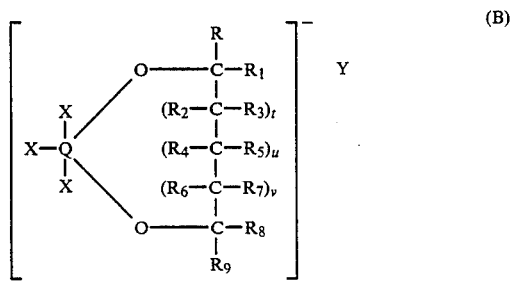

(B)

or

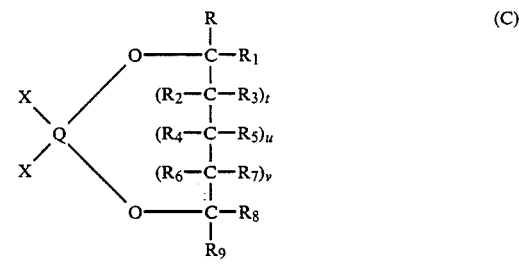

(C)

or (D) $TeO_2$ or (E) $PhTeCl_3$ or (F) $(C_6H_5)_4P^+ (TeCl_3(O_2C_2H_4))^-$ or (G) a tellurium tetrahalide.

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —$COR_{10}$ wherein $R_{10}$ is alkyl of from 1 to 5 carbons; y is a cation and X is halogen; or the pharmaceutically acceptable salts or complexes thereof. The preferred pharmaceutically acceptable salts are those wherein Y is ammonium or potassium. The complexes may be prepared by reaction of the particular compound with a pharmaceutically acceptable complexing agent which forms a water soluble complex. Suitable complexing agents include hydroxy polycarboxylic acids, polycarboxylic acids or polyhydroxy polycarboxylic acids. Generally, it is preferred to prepare the complexes by contacting a compound of Formula A-G with citric or tartaric acid and a corresponding alkali metal salt thereof such as the potassium or sodium salt. Compounds useful in the invention are described is U.S. Pat. No. 4,761,490 and in copending U.S. application Ser. No. 172,643, filed Mar. 24, 1988, both of which are incorporated by reference. The amount which is employed is sufficient to reduce the quantity of bone marrow cells which are required to establish a viable bone marrow and form modified bone cells and thereafter administering said modified cells to a host.

The tellurium derivative may be:
(a) administered to the host at the time and also before or after bone marrow transplant;
(b) added to the bone marrow in vitro prior to the administration of the bone marrow to the host; and
(c) administered to a host who has been subjected to a source of radiation.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term haloalkyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$CH_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the term alkoxy of 1 to 5 carbon atoms includes methoxy, ethoxy, n-propoxy, n-pentoxy and the like; the terms halo, halide halogen are used to signify chloro, bromo, iodo and fluoro; the term acyl includes $R_{16}CO$ wherein $R_{16}$ is H, or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2CH_3)$.

Compounds which are based on tellurium are the presently preferred compounds of the invention. The tellurium based compounds that are preferred include those of the formulas:

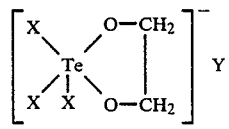

and

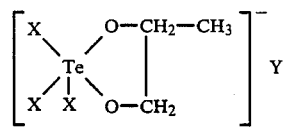

wherein X is halogen and Y is cation; such as ammonium or potassium. The preferred halogen species is chloro.

Other compounds which are based on tellurium and may be used in the practice of the invention include Ph Te $Cl_3$, Te $O_2$ and $(C_6H_5)_4$ P+ $(TeCl_3(O_2C_2H_4))^-$ (Z. Naturforsh, 36B, 307–312 (1981). The compound hereinafter described in Example 2 has the following structure:

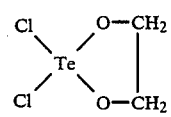

Other compounds useful for the practice of invention include:

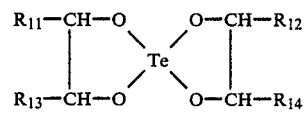

wherein $R_{11}$, $R_{12}$, $R_{13}$ and $R_{14}$ are independently selected from the group consisting of hydrogen, hydroxyalkyl of 1-5 carbon atoms, hydroxy and alkyl of 1-5 carbon atoms.

Useful dihydroxy compounds for use in the preparation of compounds of structure A or B, include those of formula I wherein R, $R_1$, $R_4$ and $R_5$ are as shown in the Table:

TABLE $$\begin{array}{c} R \quad R_4 \\ | \quad | \\ HO-C-C-OH \\ | \quad | \\ R_1 \quad R_5 \end{array} \quad (I)$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | $CH_2COOH$ | H | H |
| H | H | $CHCOOCH_3$ | H |
| H | I | H | H |
| H | H | Br | H |
| H | H | $CONH_2$ | H |
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

$$\text{HO}-\underset{R_1}{\overset{R}{C}}-\underset{R_3}{\overset{R_2}{C}}-\underset{R_5}{\overset{R_4}{C}}-\text{OH} \quad \text{(II)}$$

| R | $R_1$ | $R_2$ | $R_3$ | $R_4$ | $R_5$ |
|---|---|---|---|---|---|
| H | H | H | H | H | H |
| H | H | H | Cl | H | H |
| H | CH$_2$OH | H | H | H | H |
| H | H | H | OH | H | H |
| H | H | H | H | CH$_3$ | H |
| H | H | H | CH$_2$Cl | H | H |
| H | H | H | COOH | H | H |
| H | H | H | CH$_2$COOH | H | H |
| H | H | H | CHO | H | H |
| H | H | H | H | H | CH$_2$CHO |
| H | H | CONH$_2$ | H | H$_2$ | CH$_3$ |
| H | H | H | CN | H | H |
| H | H | H | H | CH$_2$CONH$_2$ | H |
| H | H | H | COOCH$_3$ | H$_3$ | H |
| H | H$_3$ | OCH$_3$ | H | H | H |

Other dihydroxy compounds for use in making compound of formula A and B include those of formula III wherein R, $R_1$, $R_2$, $R_3$, $R_4$ and $R_5$ are as shown in the Table.

$$\text{HO}-\underset{R_1}{\overset{R}{C}}-\underset{R_3}{\overset{R_2}{C}}-\underset{R_5}{\overset{R_4}{C}}-\underset{R_9}{\overset{R_8}{C}}-\text{OH} \quad \text{(III)}$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | OCH$_3$ | H | H | H | H | H |
| H | H$_2$ | CONH$_2$ | H | H | H | H | H |
| H | Br | H | H | Br | H | H | H |
| H | H | H | H | CH$_2$COOH | H | H | H |
| H | H | Cl | Cl | H | H | H | H |
| H | CH$_2$COOH | H | H | H | H | H | H |
| H | H | CH$_3$ | H | H | H | H | H |
| H | CH$_3$ | H | H | H | H | H | H |
| H | CH$_2$Cl | H | H | H | H | H | H |
| H | H | H | I | H | H | H | H |
| H | CH$_2$CN | H | H | H | H | H | H |
| H | H | H | H | CH$_2$CH$_2$OH | H | H | H |

Additional dihydroxy compounds include those of formula IV wherein R, $R_1$, $R_2$, $R_3$, $R_4$ and $R_5$ are as shown in the Table.

$$\text{HO}-\underset{R_1}{\overset{R}{C}}-\underset{R_3}{\overset{R_2}{C}}-\underset{R_5}{\overset{R_4}{C}}-\underset{R_7}{\overset{R_6}{C}}-\underset{R_9}{\overset{R_8}{C}}-\text{OH} \quad \text{(IV)}$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | CONCH$_3$ | H | H | H | Br | H | H | H |
| H | H | Br | H | H | H | CON(CH$_3$)$_2$ | H | H | H |
| H | H | H | OCH$_3$ | H | H | H | H | H | H |
| H | H | H | H | OCH$_3$ | H | H | H | H | H |
| H | H | H | H | CH$_2$COOH | H | H | H | H | H |
| H | H | COOH | H | H | H | H | H | H | H |
| H | CH$_3$ | H | H | H | H | H | H | H | H |
| CH$_3$ | H | H | H | H | CH$_3$ | H | H | H | H |
| H | CH$_2$CH$_3$ | H | H | H | H | H | Cl | H | H |
| H | CH$_2$CN | H | H | CH$_2$OH | H | H | H | H | H |
| H | H | H | I | H | H | H | H | CN | H |
| H | CH$_2$CH$_2$COOH | H | H | H | H | H | H | H | H |
| H | H | CHO | H | H | H | H | H | H | H |
| H | H | H | F | H | H | H | H | H | H |

The compounds of the formula:

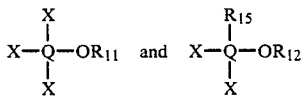

wherein $R_{11}$, $R_{12}$ and $R_{15}$ are as defined hereinabove; may be made by reacting the appropriate di, tri or tetrahaloselenide or telluride with the appropriate hydroxy compound which may be of the formula:

$$\text{HO}-R_{16}$$

$R_{16}$ is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of $R_{16}$ include methyl, ethyl, n-propyl, phenyl, tolyl, amidoethyl, cyanomethyl, methyloxymethyl and CH$_2$CH$_2$COOH.

The compounds are made by combining substantially equimolar amounts of the reactants in a suitable reactor at room temperature or at elevated temperatures up to the reflux temperature. It is preferred to utilize a solvent that is capable of dissolving the reactants such as acetonitrile, benzene, toluene, xylene, dimethylsulfoxide, mixtures thereof and the like. Compounds of structure (A) are only obtained in acetonitrile. The preferred method requires heating the reaction mixture to the reflux temperature of the solvent while stirring the reaction mixture with a suitable magnetic or mechanical stirrer. The reaction may be carried out for a sufficient period of time to ensure complete reaction of the reactants. This time will vary with the reaction conditions, the particular compound being made and the nature of the solvents. The reaction may be run at atmospheric pressure but if desired may be carried out at reduced or elevated pressure. The reaction is practically carried out in the presence of an oxygen containing atmosphere such as air but inert atmospheres such as nitrogen, argon, helium or mixtures thereof may be utilized if desired. Reaction times of 1 minute to 168 hours may be used although reaction times of 6–16 hours are preferred.

The reactor should be of glass construction or lined with glass or other ceramic material that is inert with respect to the reactants.

Usually the compounds produced in the process will precipitate as the reaction mixture is cooled to room temperature. Precipitation may also be effected by adding a suitable precipitant such as a liquid alkane such as hexane or by concentration of the reaction mixture by solvent removal by evaporation with or without the aid of vacuum. The product may be collected in a sintered glass filter, washed with a cold solvent and dried using conventional techniques. The product is stored in a suitable container, protected from light, and preferably at reduced temperature to avoid decomposition.

The solvent system for administration of the compounds of the invention may be based on dimethylsulfoxide or lower alkanols such as ethanol and propanol, glycols such as ethylene glycol, glycerol, propylene glycol and the like. A preferred solvent system is a phosphate buffered saline solution which contains an amount of sodium acid phosphate and sodium phosphate in water to give a pH of 7.1–7.2 (PBS). In addition, a citrate buffered solution may be utilized.

Those skilled in the art will appreciate that the presence of a reactive group that will interfere with the synthesis of a particular compound will require the use of a protective group that is removable using known methods.

In the examples, total body irradiation is carried out by using a radioactive $Cs^{137}$ (Gammacell 1000 apparatus) was used to deliver about 558 rads/min. Animals were positioned in irradiation chambers and exposed to a total dose of 750–850 rads 18–24 hours before bone marrow transplantation.

The following procedure was utilized to transplant the bone marrow in mice:

8–12 week old male Babl/C mice are injected intraperitoneally once or several times with a solution of 10 ug of a tellurium compound in PBS every other day. Control mice are injected with PBS. The proliferative potential of the stem-cells in the treated mice and the control mice are tested using the method of Till and McCullouch Rad. Res. 14: 213–222 (1961) and J. Cell Physiol. 69: 177–184 (1967).

The mice are sacrificed by cervical dislocation and femur bones were removed. Bone marrow is flushed from the marrow cavities with PBS using a 25-gauge needle. The cells from each group are pooled and suspended in PBS. A suitable number of viable nucleated cells in aliquots of 0.3 ml PBS are injected into the tail vein of the irradiated recipient mouse. A control group of irradiated untransplanted mice is included in each experiment. The survival of the transplanted mice is determined 11 days after bone marrow transplantation. On the eleventh day the surviving mice are sacrificed and the spleens removed and fixed in Bouins' solution. Colonies seen as distinct gray nodules embedded in the red mass of the spleen are counted using an inverted microscope or magnifying glass. Each colony (CFU-S), which represents a proliferoting stem-cell is composed of an undifferentiated population and cells from the myeloid, erythroid and megakryocytic lineages at different degrees of differentiation.

EXAMPLE

A group of donor mice were treated with 10 μg/animal of ammonium trichloro (dioxoethylene-0,0')-tellurate using the procedure set forth above. The results are summarized in Table I.

TABLE I

| | DONOR MICE | | | IRRADIATED RECIPIENT MICE (850 R) | | | |
|---|---|---|---|---|---|---|---|
| No. of Mice | No. of Injections of Active Compound | No. of Injected BM Cells | | No. of Mice in group | Survival | Colony Count Per Spleen | Mean No. of Colonies |
| Expt. 1 | | | | | | | |
| 1 | 1 | — | $4.10^4$ | 5 | 0/5 | — | |
| 1 | 2 | — | $4.10^4$ | 5 | 0/5 | — | |
| 1 | 3 | 1 | $4.10^4$ | 5 | 0/5 | — | |
| 1 | 4 | 1 | $4.10^4$ | 5 | 2/5 | 14,11 | 12.5 |
| 1 | 5 | 4 | $4.10^4$ | 5 | 3/5 | 10,10,5 | 7.5 |
| 1 | 6 | 4 | $4.10^4$ | 5 | 2/5 | 10,13 | 11.5 |
| Expt. 2 | | | | | | | |
| 1 | 7 | — | $4.10^4$ | 6 | 0/6 | — | |
| 1 | 8 | — | $4.10^4$ | 6 | 3/6 | 10,5,5 | 7 |
| 1 | 9 | 4 | $4.10^4$ | 6 | 5/6 | 10,11,18,14,6 | 12 |
| 1 | 10 | 4 | $4.10^4$ | 6 | 4/6 | 25,17,18,13 | 18 |
| 1 | 11 | 6 | $4.10^4$ | 6 | 5/6 | 26,20,23,25,23 | 23 |
| 1 | 12 | 6 | $4.10^4$ | 6 | 6/6 | 23,24,14,18,14,17 | 18 |
| Expt. 3 | | | | | | | |
| 2 | 13 + 14 | — | 6.10 | 7 | 4/7 | 23,26,1,19 | 23 |
| 2 | 15 + 16 | 4 | $6/10^4$ | 7 | 6/7 | 25,31,33,34,35 | 32 |
| 2 | 17 + 18 | — | $8/10^4$ | 7 | 6/7 | 48,28,40,36,25,27 | 34 |

The in vivo treatment of mice with ammonium trichloro (dioxoethylene-0,0')-tellurate increases the survival of irradiated mice as well as the number of spleen colonies developing from the transplanted bone marrow. Therefore, the administration of ammonium trichloro (dioxoethylene-O,O')-tellurate in conjunction with a bone marrow transplant provides a method of enhancing the reconstitution of the immune system which has been damaged by exposure to high dose chemotherapy or by exposure to radiation.

We claim:

1. A method for the transplantation of bone marrow cells said method comprising:
   (a) obtaining bone marrow cells;
   (b) contacting said bone marrow cells with an amount of a compound which is:
      (A) a source of tetravalent tellurium ions which are capable of inducing the proliferation or differentiation of bone marrow cells;

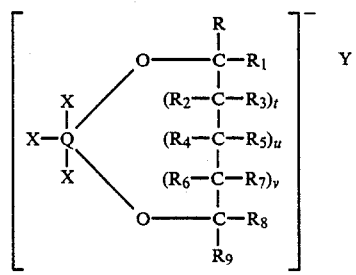

(B)

or

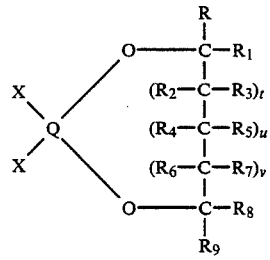

(C)

or
   (D) TeO$_2$ or
   (E) PhTeCl$_3$ or
   (F) (C$_6$H$_5$)$_4$P$^+$ (TeCl$_3$(O$_2$C$_2$H$_4$))$^-$ or
   (G) a tellurium tetrahalide$x$,
   wherein Q is Te or Se; t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —COR$_{10}$ wherein R$_{10}$ is alkyl of from 1 to 5 carbons; Y is a cation and X is halogen; or a tetravalent complex of Te or Se which is capable of inducing the proliferation or differentiation of bone marrow cells and is sufficient to reduce the quantity of bone marrow cells which are required to establish a viable bone marrow and form modified bone cells and thereafter carrying out the bone marrow transplant by transplanting said modified cells to a host.

2. A method as defined in claim 1 wherein said compound is trichloro(dioxoethylene-0,0')-tellurate.

3. A method for the transplantation of bone marrow cells which comprises:
   (a) administering to a host an amount of a compound which is:
      (A) a source of tetravalent tellurium ions which are capable of inducing the proliferation or differentiation of bone marrow cells;

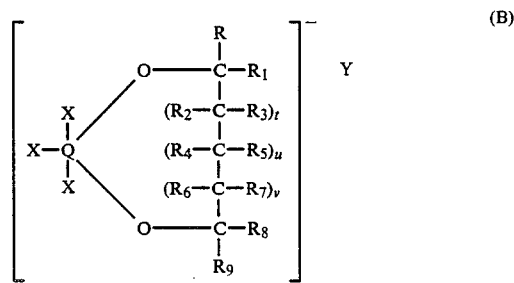

(B)

or

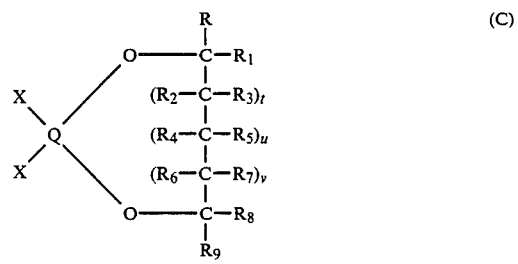

(C)

or
   (D) TeO$_2$ or
   (E) PhTeCl$_3$ or
   (F) (C$_6$H$_5$)$_4$P$^+$ (TeCl$_3$(O$_2$C$_2$H$_4$))$^-$
   (G) a tellurium tetrahalide$x$,
   wherein Q is Te or Se; t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —COR$_{10}$ wherein R$_{10}$ is alkyl of from 1 to 5 carbons; Y is a cation and X is halogen; or a tetravalent complex of Te or Se which is effective to reduce the number of bone marrow cells required for a bone marrow transplant; and
   (b) thereafter carrying out the bone marrow transplant by transplanting the modified cells to a host.

4. A method as defined in claim 3 wherein the compound is trichloro (dioxoethylene-0,0') tellurate.

5. A method of transplanting bone marrow cells which comprises:
   (a) exposing a host to a radiation source to destroy the bone marrow;

(b) administering to said host a compound of the formula:
(A) a source of tetravalent tellurium ions which are capable of inducing the proliferation or differentiation of bone marrow cells;

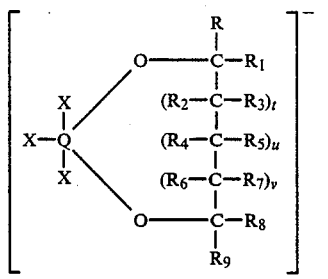 (B)

or

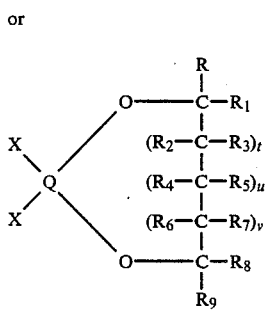 (C)

or
(D) TeO$_2$ or
(E) PhTeCl$_3$ or
(F) (C$_6$H$_5$)$_4$P$^+$ (TeCl$_3$(O$_2$C$_2$H$_4$))$^-$
(G) a tellurium tetrahalidex, wherein Q is Te or Se; t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —COR$_{10}$ wherein R$_{10}$ is alkyl of from 1 to 5 carbons; Y is a cation; and X is halogen; or a tetravalent complex of Te or Se which is capable of inducing the proliferation or differentiation of bone marrow cells and an amount of bone marrow cells which is sufficient to establish a functioning bone marrow and thereafter carrying out the bone marrow transplant by transplanting the modified bone marrow cells to a host.

6. A method as defined in claim 5 wherein the compound is ammonium trichloro (dioxoethylene-0,0') tellurate.

* * * * *